US00PP28073P3

(12) United States Plant Patent
Meilland

(10) Patent No.: US PP28,073 P3
(45) Date of Patent: Jun. 6, 2017

(54) *FLORIBUNDA* ROSE PLANT NAMED 'MEIDOSCOPE'

(50) Latin Name: *Rosa hybrida*
Varietal Denomination: Meidoscope

(71) Applicant: CP DELAWARE, INC., Wilmington, DE (US)

(72) Inventor: Alain A. Meilland, Antibes (FR)

(73) Assignee: The Conard-Pyle Company, West Grove, PA (US)

( * ) Notice: Subject to any disclaimer, the term of this patent is extended or adjusted under 35 U.S.C. 154(b) by 162 days.

(21) Appl. No.: 14/756,065

(22) Filed: Jul. 28, 2015

(65) Prior Publication Data

US 2017/0034973 P1 Feb. 2, 2017

(51) Int. Cl.
*A01H 5/02* (2006.01)

(52) U.S. Cl.
USPC ..... Plt./142

(58) Field of Classification Search
USPC ..... Plt./101, 141
See application file for complete search history.

*Primary Examiner* — Susan McCormick Ewoldt
*Assistant Examiner* — Karen Redden
(74) *Attorney, Agent, or Firm* — Buchanan Ingersoll & Rooney PC

(57) ABSTRACT

A new and distinct Floribunda rose plant is provided that forms abundantly and substantially continuously attractive cup-shaped semi-double blossoms that are orange suffused with pink and yellow in coloration. The growth habit is compact and bushy. Vigorous vegetation is formed. Such vegetation is ornamental dark green and bears a glossy aspect on the upper surface. The plant is well suited for providing attractive ornamentation in parks and gardens. The plant can be grown well in containers in view of its compact character, grows well on its own roots, and is well suited for growing in the relatively dry climate of the west coast of the United States. The blossoms commonly are displayed from spring to the time of frost.

1 Drawing Sheet

Botanical/commercial classification: *Rosa hybrida*/Floribunda Rose Plant.

Varietal denomination: cv. Meidoscope.

SUMMARY OF THE INVENTION

The new variety of *Rosa hybrida* Floribunda rose plant was created by artificial pollination during June 2004 at Le Luc in Provence, France, wherein two parents were crossed which previously had been studied in the hope that they would contribute the desired characteristics. The female parent (i.e., the seed parent) was the 'KORfalt' variety (non-patented in the United States). The 'KORfalt' variety is protected in Germany under No. 711,432. The male parent (i.e., the pollen parent) was the 'MACivy' variety (U.S. Plant Pat. No. 8,362).

The parentage of the new variety can be summarized as follows:

'KORfalt'×'MACivy'.

The seeds resulting from the above pollination were sown and small plants were obtained which were physically and biologically different from each other. Selective study resulted in the identification of a single plant of the new variety.

It was found that the new Floribunda rose plant of the present invention:

(a) displays a compact and bushy growth habit with vigorous vegetation,
(b) forms abundantly and substantially continuously attractive cup-shaped semi-double blossoms that are orange suffused with pink and yellow in coloration, (c) exhibits ornamental dark green foliage with a glossy aspect on the upper surface, and
(d) is well suited for providing attractive ornamentation in parks and gardens.

The new variety well meets the needs of the horticultural industry and can be grown to advantage in parks and gardens, public areas, and residential landscapes where ornamentation is to be provided. The new plant can be grown well in containers in view of its compact character. The dark green vegetation is vigorous, and strong. Blossoms commonly are displayed from spring to the time of frost. The new plant is particularly well suited for growing in the relatively dry climate on the west coast of the United States, and grows well on its own roots.

The new variety can be readily distinguished from its ancestors. For instance, the 'KORfalt' variety bears double flowers of deep gold yellow coloration with significantly heavier petalage (i.e., about 25 to 30 petals), and the 'MACivy' variety forms blossoms of a dissimilar apricot coloration also having a greater number of petals.

The new variety of the present invention also readily distinguished from other previously available Floribunda rose varieties, such as the 'Wekvossutono' variety (U.S. Plant Pat. No. 18,473). For instance, the blossoms of the 'Wekvossutono' variety are very double with about 30 to 45 petals and about 5 and 9 petaloids.

The new variety has been found to undergo asexual propagation at Wasco, Calif., U.S.A., by a number of routes, including budding, grafting, and the use of cuttings. Asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meidoscope' and will be marketed under the POLYNESIAN PUNCH Trademark.

BRIEF DESCRIPTION OF THE PHOTOGRAPH

The accompanying photograph shows as nearly true as it is reasonably possible to make the same, in a color illustration of this character, typical specimens of buds, blossoms, and foliage of the new variety. The rose plants of the new variety were approximately two years of age and were observed during October 2014 while growing on their own roots outdoors at Wasco, Calif., U.S.A.

DETAILED BOTANICAL DESCRIPTION

The chart used in the identification of the colors is that of The Royal Horticultural Society (R.H.S. Colour Chart—1995). The description is based on the observation of two-year-old plants during May while growing outdoors on their own roots at West Grove, Pa., U.S.A.

Class: Floribunda.

Plant:

*Growth habit*.—Compact and bushy.

*Height*.—Approximately 1.35 m on average.

*Width*.—Approximately 90 cm on average.

Branches:

*Length*.—Main stems: approximately 30 cm on average. Secondary stems: approximately 10 cm on average.

*Color*.—Young stems: near Green Group 137D. Adult wood: near Yellow-Green Group 146B.

*Thorns*.—Young: commonly approximately 8 mm in length on average, approximately 6 mm in width on average at the point of attachment, and near Yellow-Green Group 152B in coloration. Mature: commonly approximately 6 mm in length on average, approximately 4 mm in width on average at the point of attachment, and near Brown Group 200C in coloration.

Leaves:

*Size*.—A five-leaflet leaf commonly is approximately 13.5 cm in length on average, and approximately 8.5 cm in width on average.

*Leaflets*.—Number: 3, 5 and 7. Shape: generally ovate. Size: the terminal leaflets commonly are approximately 5 cm in length on average, and approximately 3.5 cm in width on average, and the lower leaflets commonly are approximately 4.5 cm in length on average, and approximately 2 cm in width on average. Margins: serrate. Texture: glabrous and glossy upper surface, and smooth on the under surface. Color (young foliage): Upper surface: near Green Group 138A. Under surface: near Green Group 139C. Color (mature foliage): Upper surface: near Green Group 137A. Under surface: near Yellow-Green Group 147B.

Inflorescence:

*Number of flowers*.—Commonly approximately 8 to 15 blossoms per stem, and approximately 50 blossoms on average on a plant at a given time.

*Peduncle*.—Glandular, approximately 7 cm in length on average, approximately 3 mm in diameter on average, often pubescent, and near Green Group 143C in coloration.

*Sepals*.—Number: 5. Upper surface: smooth with short pubescence, and near Green Group 138B in coloration. Under surface: smooth with grayish white pubescence, and near Green Group 138A in coloration. Size: approximately 2.5 cm in length on average, and approximately 8 mm in width at the widest point on average. Margin: entire, commonly two or three sepals having extensions of approximately 5 mm in length and approximately 1 mm in width.

*Buds*.—Shape: substantially conical. Length: approximately 2.5 cm on average. Width: approximately 1.5 cm on average at the widest point. Color as calyx breaks: commonly near Orange Group 26B towards the apex blending to Red Group 39B at the base.

*Flower*.—Shape: cup-shaped. Size: when open commonly approximately 6 cm in width on average, and approximately 4 cm in depth on average. Color (in the course of opening): Upper surface: near Yellow Group 12A at the point of attachment, and blending to near Orange Group 25D towards the apex. Under surface: near Yellow Group 12B at the point of attachment, and blending to near Orange Group 24C towards the apex. Color: (at the end of blooming): Upper side: near Yellow Group 11A blending to near Red Group 55A towards the apex. Under side: near Yellow Group 4B blending to near Red Group 55B towards the apex. Fragrance: none detected. Petal number: commonly approximately 17 on average under normal growing conditions. Petal shape: with an obcordate tip and an ovate base. Petal margin: entire and wavy. Petal length: approximately 3.5 cm on average. Petal width: approximately 3 cm on average. Petal arrangement: imbricated. Petal drop: good with the petals commonly detaching cleanly before drying. Stamen number: approximately 100 on average. Anthers: regularly arranged around the styles, and near Yellow-Orange Group 22A in coloration. Filaments: approximately 5 mm in length on average, and near Yellow Group 12A in coloration. Pollen: commonly present in a moderate quantity, and near Yellow-Orange Group 22A in coloration. Pistils: separate and free, approximately 75 in number on average. Stigmas: approximately 0.5 mm in diameter on average, and near Yellow Group 2B in coloration. Styles: approximately 7 mm in length on average, and near Yellow Group 2C in coloration. Receptacle: smooth, achenes stand on the bottom and wall, approximately 1 cm in length on average, approximately 7 mm in diameter on average, and near Green Group 143B in coloration. Hips: none available for observation.

Development:

*Vegetation*.—Dark green, vigorous and strong.

*Blooming*.—Abundant and substantially continuous from spring to frost in the fall.

*Disease resistance*.—During observations to date is considered to be average with respect to black spot, mildews, and rust.

The new 'Meidoscope' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a compact and bushy growth habit with vigorous vegetation, (b) forms abundantly and substantially continuously attractive cup-shaped semi-double blossoms that are orange suffused with pink and yellow in coloration, (c) exhibits ornamental dark green foliage with a glossy aspect on the upper surface, and (d) is well suited for providing attractive ornamentation in parks and gardens;

substantially as shown and described.

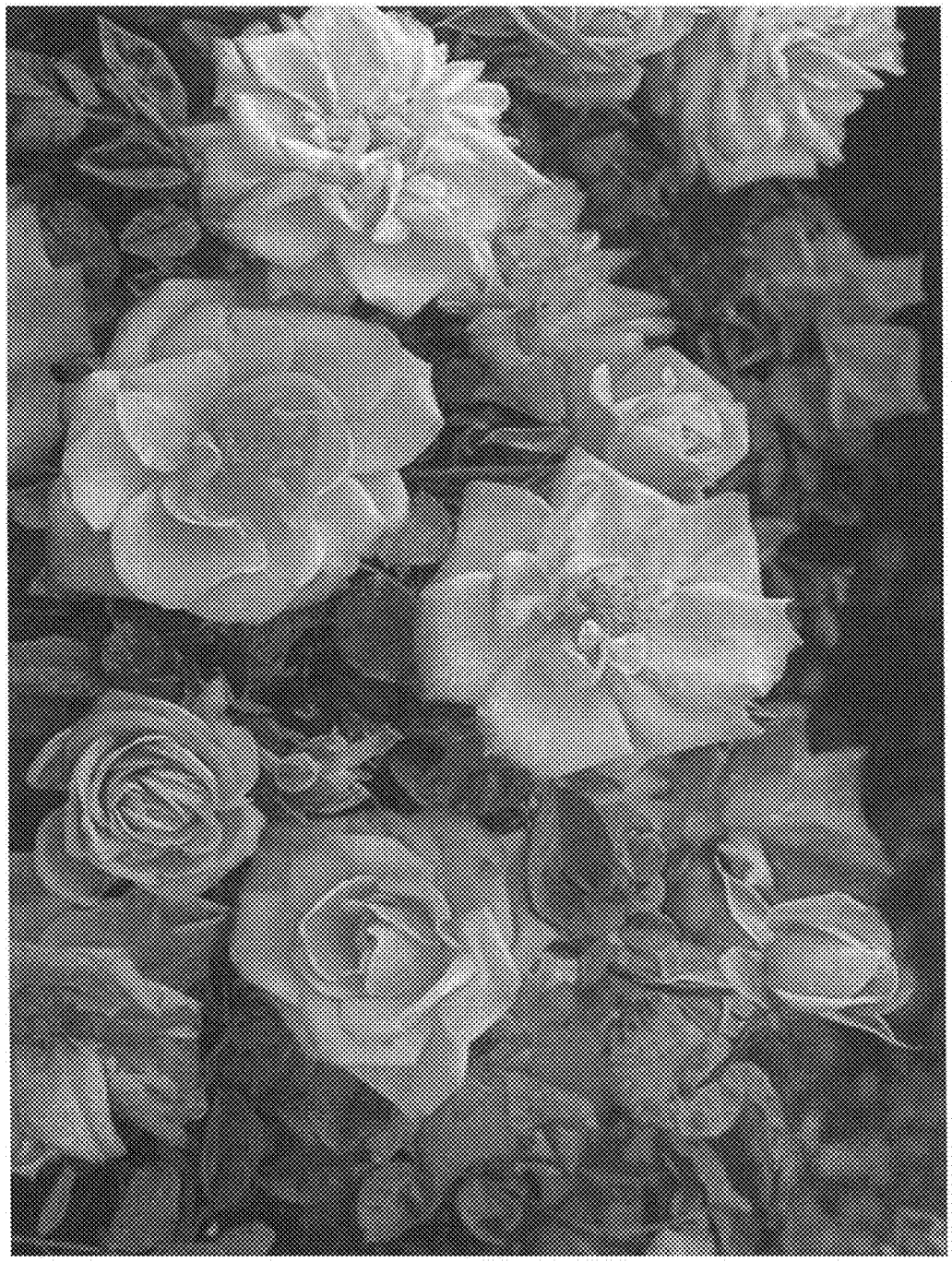

* * * * *